(12) United States Patent
Hwang et al.

(10) Patent No.: US 10,429,319 B2
(45) Date of Patent: Oct. 1, 2019

(54) INSPECTION SYSTEM INCLUDING PARALLEL IMAGING PATHS WITH MULTIPLE AND SELECTABLE SPECTRAL BANDS

(71) Applicant: KLA-Tencor Corporation, Milpitas, CA (US)

(72) Inventors: Shiow-Hwei Hwang, San Ramon, CA (US); Amir Bar, Santa Clara, CA (US); Grace Hsiu-Ling Chen, Los Gatos, CA (US); Daniel L. Cavan, Woodside, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 788 days.

(21) Appl. No.: 14/215,580

(22) Filed: Mar. 17, 2014

(65) Prior Publication Data

US 2014/0285657 A1 Sep. 25, 2014

Related U.S. Application Data

(60) Provisional application No. 61/803,622, filed on Mar. 20, 2013.

(51) Int. Cl.
*H04N 9/47* (2006.01)
*G01N 21/95* (2006.01)
*G01N 21/88* (2006.01)

(52) U.S. Cl.
CPC ..... *G01N 21/9501* (2013.01); *G01N 21/8806* (2013.01); *G01N 2021/8845* (2013.01)

(58) Field of Classification Search
CPC .. G01N 2021/8845; G06T 2207/30148; H01L 2924/0002; H01L 2924/00
(Continued)

(56) References Cited

U.S. PATENT DOCUMENTS 5,455,870 A 10/1995 Sepai et al.
2002/0044277 A1* 4/2002 Yonezawa ........ G01N 21/95623
356/237.2
(Continued)

FOREIGN PATENT DOCUMENTS

TW I276147 B 3/2007

OTHER PUBLICATIONS

Office Action dated Jan. 23, 2018 for Taiwan Patent Application No. 103110536.

*Primary Examiner* — Jamie J Atala
*Assistant Examiner* — Masum Billah
(74) *Attorney, Agent, or Firm* — Suiter Swantz pc llo

(57) ABSTRACT

The present disclosure is directed to a system for inspecting a sample with multiple wavelengths of illumination simultaneously via parallel imaging paths. The system may include at least a first detector or set of detectors configured to detect illumination reflected, scattered, or radiated along a first imaging path from a selected portion of the sample in response to the first wavelength of illumination and a second detector or set of detectors configured to concurrently detect illumination reflected, scattered, or radiated along a second imaging path from the selected portion of the sample (i.e. the same location on the sample) in response to the second wavelength of illumination, where the second imaging path may at least partially share illumination and/or detection optics with an autofocus channel.

32 Claims, 14 Drawing Sheets

(58) Field of Classification Search
USPC .......................................................... 348/125
See application file for complete search history.

(56) References Cited

U.S. PATENT DOCUMENTS

| | | | |
|---|---|---|---|
| 2002/0054291 A1* | 5/2002 | Tsai ................... | G01N 21/8806 |
| | | | 356/394 |
| 2004/0235205 A1* | 11/2004 | Levy ................... | G01N 21/211 |
| | | | 438/14 |
| 2005/0085032 A1 | 4/2005 | Aghababazadeh et al. | |
| 2007/0121106 A1* | 5/2007 | Shibata .............. | G01N 21/8806 |
| | | | 356/237.2 |
| 2008/0075353 A1 | 3/2008 | Tek et al. | |
| 2009/0278934 A1 | 11/2009 | Ecker et al. | |
| 2010/0033716 A1 | 2/2010 | Tsai et al. | |
| 2012/0050739 A1* | 3/2012 | Hayano ................. | G01B 11/24 |
| | | | 356/369 |

\* cited by examiner

INSPECTION SYSTEM INCLUDING PARALLEL IMAGING PATHS WITH MULTIPLE AND SELECTABLE SPECTRAL BANDS

PRIORITY

The present application claims priority under 35 U.S.C. § 119(e) to U.S. Provisional Patent Application Ser. No. 61/803,622, entitled INSPECTION APPARATUS WITH MULTIPLE AND SELECTABLE BANDS SIMULTANEOUSLY, By Shiow-Hwei Hwang et al., filed Mar. 20, 2013, which is currently, or is an application of which currently application(s) are entitled to the benefit of the filing date. The above-referenced provisional patent application is hereby incorporated by reference in its entirety.

TECHNICAL FIELD

The present disclosure generally relates to the field of inspection systems and more particularly to autofocus and imaging paths within an inspection system.

BACKGROUND

As semiconductor devices continue to be manufactured on smaller scales, inspection systems are required to detect and analyze sample defects of interest (DOI) with increased accuracy and precision. Often a sample, such as a wafer or a reticle, is imaged multiple times to generate more data, which can be processed (i.e. combined and/or compared) to filter out nuisance and isolate data associated with DOI. When the sample is imaged multiple times, possibly using different illumination wavelength and/or aperture settings, throughput is reduced. Moreover, machine drifts or vibrations can offset the inspected location on the sample from run to run and complicate alignment of the sample images due to lack of clear and/or similar features. This alignment uncertainty, as well as temporal fluctuations in the imaging system, increases inspection noise and reduces the benefits of multi-wavelength inspection.

SUMMARY

In one aspect, this disclosure is directed to a system for inspecting a sample with multiple wavelengths of illumination simultaneously via parallel imaging paths. Because the same location is imaged concurrently with two or more wavelengths and/or polarizations, the collected imaging data includes different parameters that can be analyzed to differentiate nuisance components of the images from those attributable to one or more sample defects of interest (DOI). For example, several image components may be labeled as defects. However, only some of the labeled defects are DOI, while the others are nuisances. The images are easily aligned because they are collected simultaneously with one inspection pass; hence, the alignment is not complicated by offsets due to machine drift and/or vibrations. In some embodiments, the system includes one or more illumination sources configured to illuminate at least a portion of a surface of a sample simultaneously with at least a first wavelength of illumination and a second wavelength of illumination. For example, the system may include a first illumination source configured to illuminate at least a portion of a surface of a sample with a first wavelength of illumination and a second illumination source configured to illuminate at least a portion of the surface of the sample with a second wavelength of illumination that is different from the first wavelength of illumination. The system may further include at least a first detector or set of detectors configured to detect illumination reflected, scattered, or radiated along a first imaging path from a selected portion of the sample in response to the first wavelength of illumination and a second detector or set of detectors configured to detect illumination reflected, scattered, or radiated along a second imaging path from the selected portion of the sample (i.e. the same location on the sample) in response to the second wavelength of illumination. The system may further include an autofocus module configured to detect illumination reflected scattered, or radiated from the selected portion of the sample along a third imaging path in response to a third wavelength of illumination, which may be close to the second wavelength of illumination. The second and third wavelengths of illumination may be longer than the first wavelength of illumination, and in some embodiments, the autofocus channel is at least partially used to provide the second wavelength of illumination. A computing system communicatively coupled with the first detector and the second detector may be configured to receive imaging data from the first detector and imaging data from the second detector collected via the first imaging path and the second imaging path, respectively. The computing system may be further configured to process the imaging data collected via the first and second imaging paths to detect and/or analyze at least one sample DOI. For example, the computing system may be configured to locate the sample DOI by filtering out imaging data attributable to nuisance and may be further configured to size and/or classify the DOI.

In another aspect, this disclosure is directed to a method of inspecting a sample with multiple wavelengths of illumination, including at least the steps of: illuminating at least a portion of a surface of a sample simultaneously with at least a first wavelength of illumination and a second wavelength of illumination, the second wavelength of illumination being different from the first wavelength of illumination; detecting illumination reflected, scattered, or radiated along a first imaging path from a selected portion of the sample in response to the first wavelength of illumination; detecting illumination reflected, scattered, or radiated along a second imaging path from the selected portion of the sample in response to the second wavelength of illumination; and comparing imaging data collected via the first imaging path and imaging data collected via the second imaging path to differentiate a portion of the imaging data collected via the first imaging path and the imaging data collected via the second imaging path that is attributable to nuisance from a portion of the imaging data collected via the first imaging path and the imaging data collected via the second imaging path that is attributable to a sample DOI.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings. FIGS. 1A through 4D generally illustrate a system and method for inspecting a sample, such as a wafer or a reticle, with multiple wavelengths of illumination simultaneously via parallel imaging paths. As used throughout the present disclosure, the term "wafer" generally refers to a substrate formed of a semiconductor or non-semiconductor material. For example, a semiconductor or non-semiconductor material may include, but is not limited to, monocrystalline silicon, gallium arsenide, and indium phosphide. A wafer may include one or more layers. For example, such layers may include, but are not limited to, a resist, a dielectric material, a conductive material, and a semiconductive material. Many different types of such layers are known in the art, and the term wafer as used herein is intended to encompass a wafer on which all types of such layers may be formed. Parallel imaging allows the same location or closely adjacent locations on the sample within the field of view (FOV) of the objective lens to be imaged concurrently with two or more wavelengths and/or polarizations. Accordingly, the collected imaging data includes different parameters that can be analyzed to differentiate nuisance components of the images from those attributable to sample defects of interest (DOI). In addition, the images collected in parallel may be easier to align because the images are collected simultaneously with one inspection pass; hence, the alignment is not complicated by offsets due to machine drift and/or vibrations.

Figure 1A:
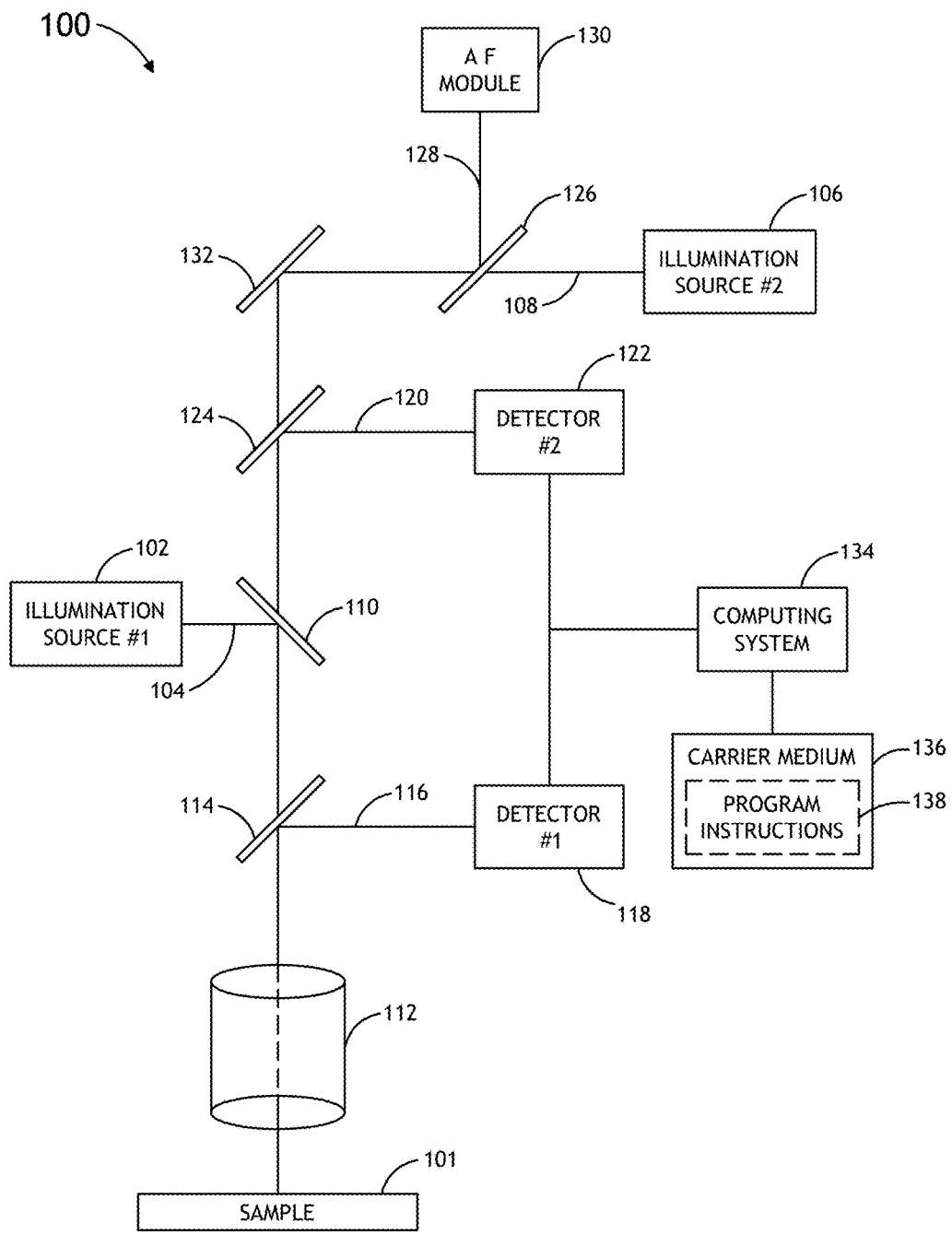
FIG. 1A is a block diagram illustrating a system for inspecting a sample with multiple wavelengths of illumination simultaneously via parallel imaging paths, in accordance with an embodiment of this disclosure.

Looking now to FIG. 1A, an inspection system 100 for detecting and/or analyzing one or more DOI of a sample 101 is illustrated in accordance with an embodiment of this disclosure. The system 100 includes one or more illumination sources configured to illuminate at least a portion of the sample 101 with at least a first wavelength or band of illumination and a second wavelength or band of illumination. For example, the system 100 may include a first illumination source 102 configured to illuminate at least a portion of a surface of a sample 101 with a first wavelength or band of illumination via a first illumination path 104 and a second illumination source 106 configured to illuminate at least a portion of the surface of the sample with a second wavelength or band of illumination that is different from the first wavelength of illumination via a second illumination path 108. At least one of the sources 102/106 may be a broadband illumination source, or in some embodiments, both sources 102 and 106 may be broadband sources. In some embodiments, the first illumination source 102 and/or the second illumination source 106 may be tunable or may include a set of selectable sources or filters to allow for selection of the first wavelength or range of wavelengths and/or the second wavelength or range of wavelengths from a first spectral band and a second spectral band, respectively, where the first and second spectral bands are different from one another. For example, the first and second wavelengths or spectral bands may be separated by at least 300 nanometers (nm).

In some embodiments, the system 100 further includes a dichroic combiner 110 configured to direct illumination provided by the first illumination source 102 along the first illumination path 104 and illumination provided by the second illumination source 106 along the second illumination path 108 along a common illumination path leading to the surface of the sample 101. Accordingly, a selected portion of the sample 101 may be imaged simultaneously with the first and second wavelengths or bands of illumination through one objective lens assembly 112. Illumination reflected, scattered, or radiated from the sample 101 may be directed through the objective 112 to at least one splitter/combiner 114 (e.g. 50/50 for the first wavelength and high transmission for the second wavelength) configured to direct illumination reflected, scattered, or radiated from the sample 101 in response the first wavelength of illumination along a first imaging path 116 to a first detector 118 or set of detectors (e.g. at least one CCD camera or photo-sensor array) and illumination reflected, scattered, or radiated from the sample 101 in response to the second wavelength of illumination along a second imaging path 120 to a second detector 122 or set of detectors.

The system may further include a splitters 124 (e.g. 50/50 splitter) and a dichroic splitter/combiner 126 configured to direct illumination reflected, scattered, or radiated from the sample 101 in response to a third wavelength or band of illumination along a third imaging path 128 to an autofocus (AF) module 130, which may be configured for pre-inspection of the sample with pre-mapping methodology. The second and third wavelengths of illumination may be close to one another (i.e. within the same spectral band or similar spectral bands) and may be longer than the first wavelength of illumination. In some embodiments, at least a portion of the AF channel is utilized to provide the second wavelength of illumination. For example, the second illumination source 106 may be configured to provide the second and third wavelengths of illumination along a common illumination path 108. Those skilled in the art will further appreciate that the illumination and/or imaging paths may include or may be further delineated according to additional optical elements, such as lenses, optical fibers, diffractive elements, prisms, polarization elements, mirrors, and the like. For example, as shown in FIG. 1A, the system 100 may further include a folding mirror 132 configured to direct illumination from the second illumination path through the 50/50 splitter/combiner 114 to the sample 101 and further configured to direct illumination reflected, scattered, or radiated from the sample 101 in response to the third wavelength/band of illumination to the third imaging path 128 via a dichroic splitter/combiner 126.

Figure 1B:
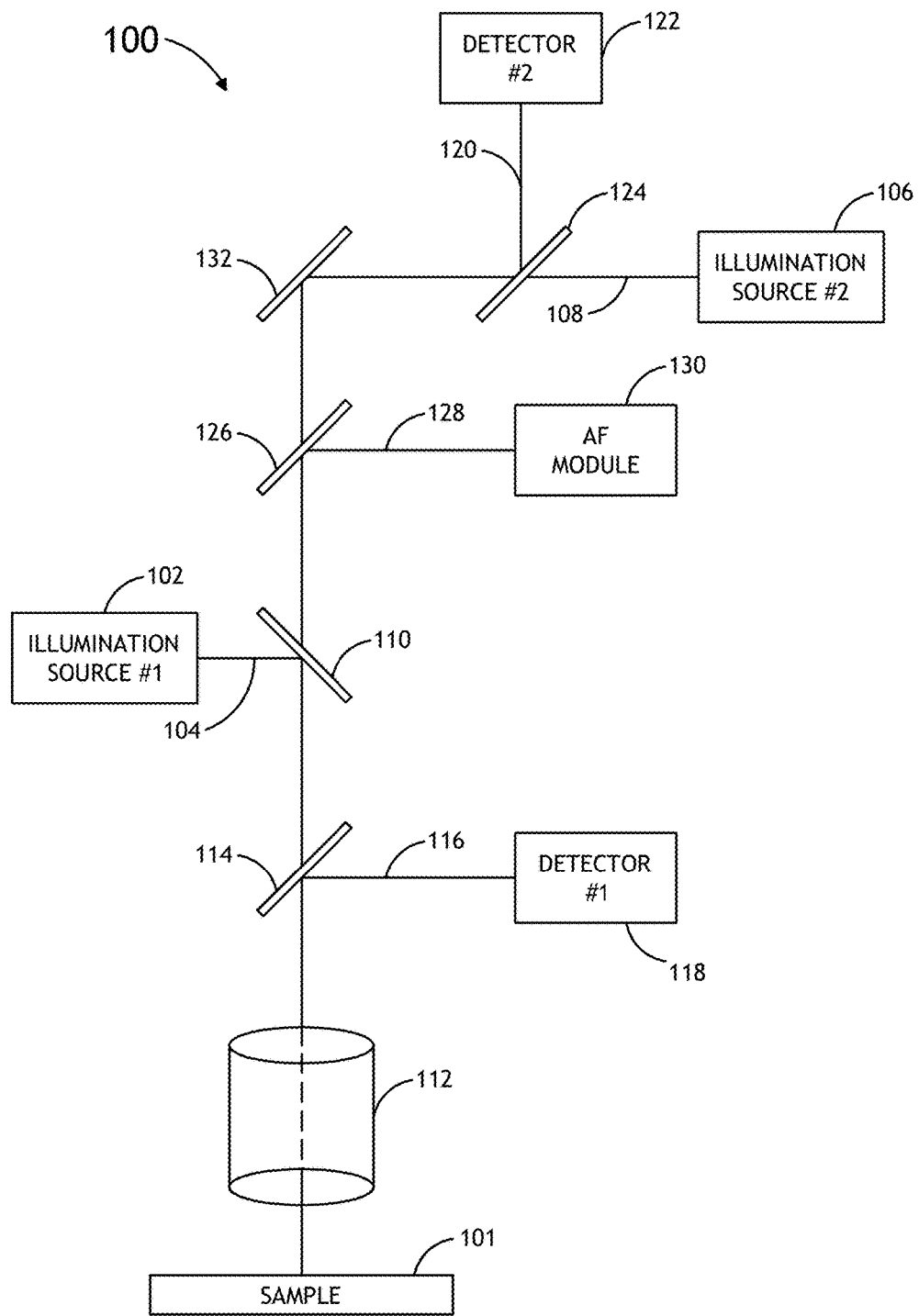
FIG. 1B is a block diagram illustrating a system for inspecting a sample with multiple wavelengths of illumination simultaneously via parallel imaging paths, in accordance with an embodiment of this disclosure.
Figure 1C:
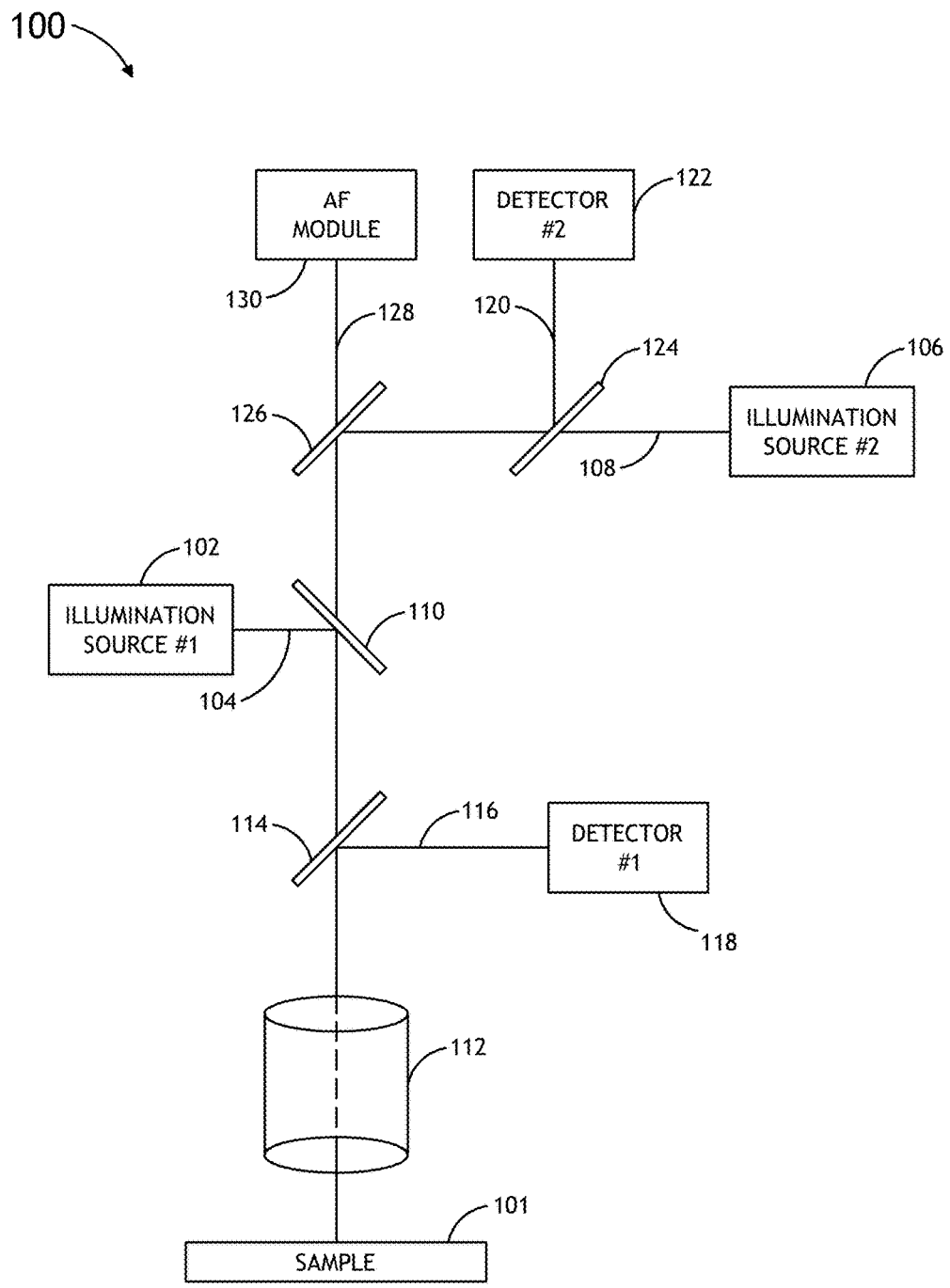
FIG. 1C is a block diagram illustrating a system for inspecting a sample with multiple wavelengths of illumination simultaneously via parallel imaging paths, in accordance with an embodiment of this disclosure.
Figure 1D:
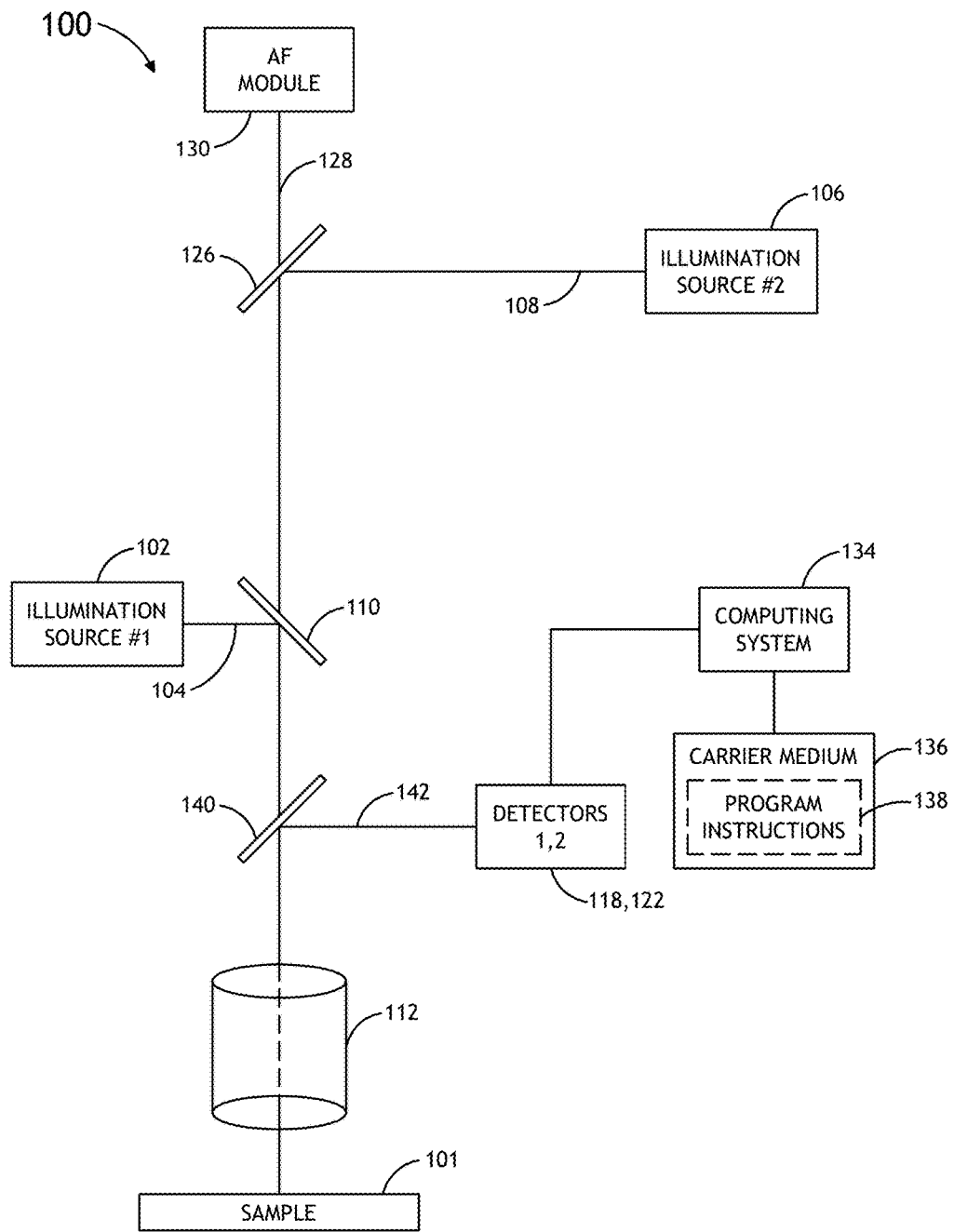
FIG. 1D is a block diagram illustrating a system for inspecting a sample with multiple wavelengths of illumination simultaneously via parallel imaging paths, in accordance with an embodiment of this disclosure.

FIGS. 1B through 1D illustrate alternative embodiments of system 100. In an embodiment shown in FIG. 1B, the second imaging path 120 leading to the second detector 122 and the third imaging path 128 leading to the autofocus module 130 are switched around. In an embodiment shown in FIG. 1C, the second wavelength and the third wavelength may be similar, and the second imaging path 120 and the third imaging 128 may be combined close to the intermediate field conjugate. Accordingly, the autofocus channel and the second wavelength channel may be configured to illuminate and image the sample at different locations. In such embodiments, splitter/combiner 126 may be spatially transmissive for the autofocus field and reflective for the second wavelength.

Figure 1E:
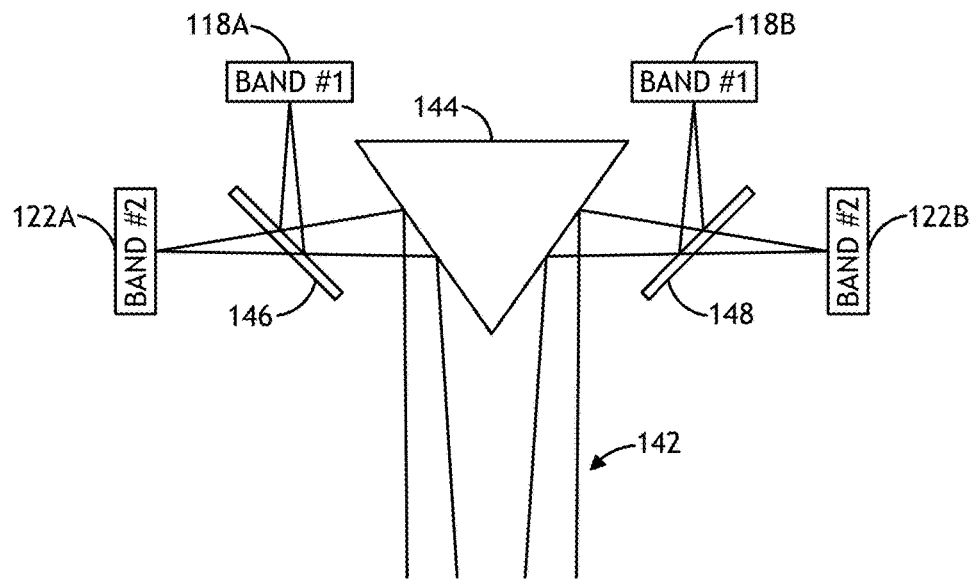
FIG. 1E is a block diagram illustrating a common detection configured to output detected illumination to a plurality of parallel imaging paths, in accordance with an embodiment illustrated in FIG. 1D.
Figure 1F:
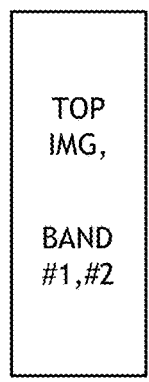
FIG. 1F illustrates a field at a sample plane, in accordance with an embodiment illustrated in FIG. 1E.
Figure 1F:
Figure 1G:
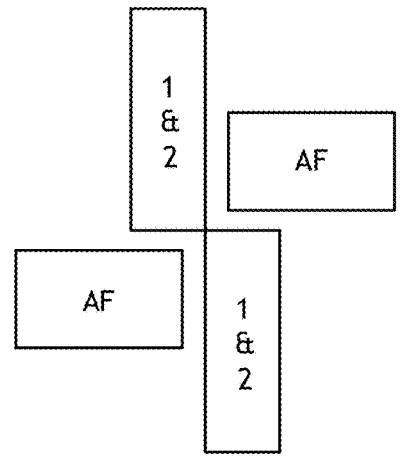
FIG. 1G illustrates a field at an image plane, in accordance with an embodiment illustrated in FIG. 1E.

FIG. 1D illustrates an embodiment of system 100 where a splitter/combiner 140 directs illumination collected through the objective 112 along a common detection path 142 to the detectors 118 and 122. As shown in FIG. 1E, the detection path 142 include a prism 144 configured to split illumination reflected, scattered, or radiated from the sample 101 into first and second portions (e.g. top left and bottom right portions) images which are collected in parallel via respective paths delineated by (dichroic) splitters 146 and 148 by a first set of detectors 118A and 118B in response to the first wavelength or band of illumination and a second set of detectors 122A and 122B in response to the second wavelength or band of illumination. FIG. 1F shows the corresponding field at the sample plane, and FIG. 1G shows the corresponding field at the image plane, wherein AF field is at different location from the inspection (first and second wavelength) field.

The system 100 may further include a computing system 134 communicatively coupled with the first detector 118 and the second detector 122 and configured to receive imaging data collected in parallel from the selected portion of the sample 101 via the first and second imaging paths 116 and 120. As used herein, the term "communicatively coupled" may refer to a direct (wired) connection, a wireless connection, and/or a networked or switched connection for receiving imaging data from the detectors 118 and 122. In some embodiments, the computing system 134 may be detached from the detectors 118 and 122 and alternatively configured to receive the imaging data via a portable carrier medium, such as a flash drive or an external hard drive. The system 100 may further include a plurality of communicatively coupled or detached computing systems 134 configured to jointly perform the steps, functions, or operations performed by the "computing system 134" described herein. Those skilled in the art will appreciate that any number and/or arrangement of computing systems 134 can be utilized without departing from the scope of this disclosure.

The computing system 134 may perform the various functions or operations described herein according to program instructions 138 executed by at least one processor of the computing system 134 from a communicatively coupled carrier medium 136. The program instructions 138 may further include an instruction set implementing the steps, functions, and/or operations described below with regard to method 400. According to various embodiments, the computing system 134 is configured to process the imaging data collected via the first imaging path 116 and the imaging data collected via the second imaging path 120 to detect and/or analyze one or more DOI of the sample 101. For example, the computing system 134 may be configured to combine and/or compare the imaging data collected via the first and second imaging paths 116 and 120 to determine a location, spatial parameter (e.g. length, width, and/or depth), and/or classification of at least one sample DOI.

In some embodiments, the computing system 134 may be configured to compare imaging data collected via the first imaging path 116 and imaging data collected via the second imaging path 120 to differentiate portions of the imaging data attributable to nuisance from portions of the imaging data attributable to DOI. For example, images collected via the first and second paths 116 and 120 may include similar components resulting from the DOI, while nuisance components may differ from image to image as a result of the different wavelengths or bands associated with each imaging path. The computing system 134 may fuse the imaging data collected via each of the imaging paths into a combined image, where the DOI component is more easily distinguishable from the nuisance due to averaging or weighting. The computing system 134 may be further configured to exclude a portion of the imaging data that is identified as being attributable to nuisance from the fused imaging data.

Figure 2A:
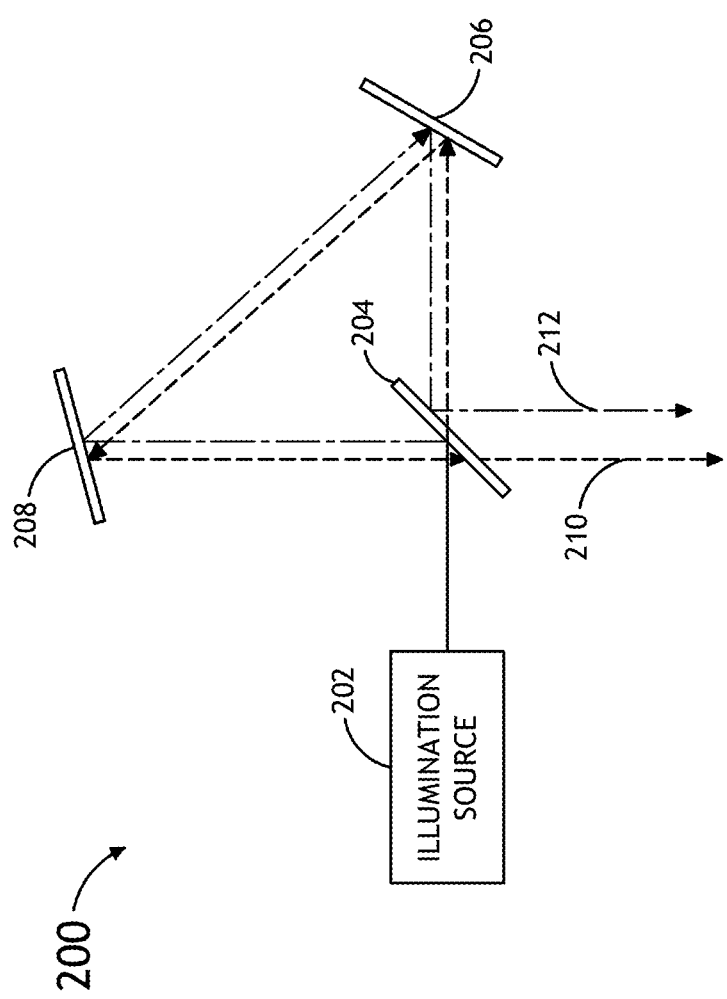
FIG. 2A is a block diagram illustrating a multiple-mode illumination path, in accordance with an embodiment of this disclosure.
Figure 2C:
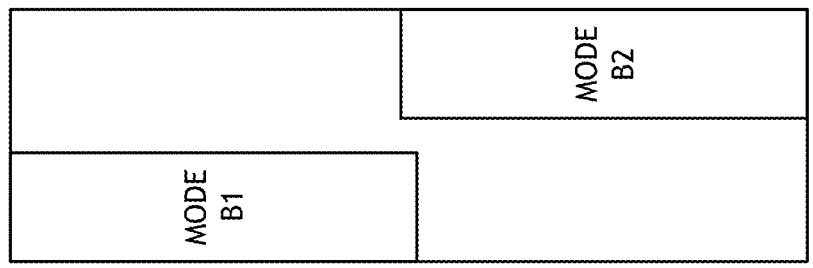
FIG. 2C illustrates a field at an image plane, in accordance with an embodiment illustrated in FIG. 2A.
Figure 2C:
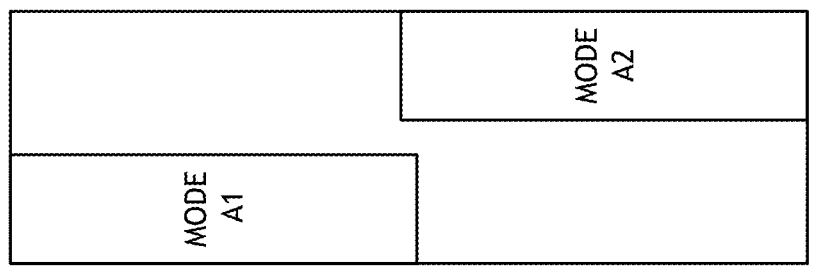
Figure 2B:
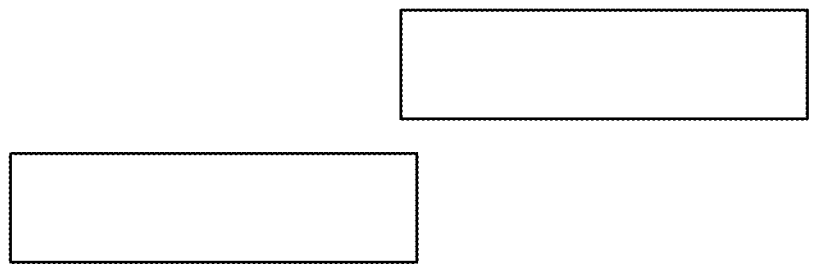
FIG. 2B illustrates a field at a sample plane, in accordance with an embodiment illustrated in FIG. 2A.

Each of the illumination paths 104 and 108 may be further configured to provide multiple imaging modes based upon different wavelengths of illumination, polarizations, aperture settings or the like. For example, as shown in FIG. 2A, an illumination path 200 may direct illumination emanating from an illumination source 202 according to at least a first mode and a second mode utilizing a dichroic and/or polarized beam splitter 204 to further split illumination emanating from the illumination source 202 according to a cutoff wavelength (i.e. subsets of the first or second spectral bands) and/or according to polarization. In some embodiments, the beam splitter 204, a first folding mirror 206, and a second folding mirror 208 are arranged in a non-isosceles triangle to direct illumination transmitted through the beam splitter 204 along a first beam path 210 and illumination reflected from the beam splitter 204 along a second beam path 212. The first imaging path 116 and the second imaging path 120 may further include optics, such as prisms and/or mirrors, configured to direct the resulting beams to a first set of detectors 118 and a second set of detectors 122. Accordingly, the imaging paths 116 and 120 may be configured to concurrently image the selected portion of the sample 101 utilizing four imaging modes (i.e. two imaging modes for the first wavelength or band of illumination and two imaging modes for the second wavelength or band of illumination). FIGS. 2B and 2C illustrate exemplary fields at the sample plane and at the image plane, respectively, as a result of the multiple-mode imaging configuration. With imaging data collected in parallel utilizing four modes at similar location and timing, alignment is maintained while further improving throughput, DOI detection and analysis, and/or nuisance reduction due to the different wavelengths or bands of illumination and any other imaging parameters associated with each mode.

Figure 3A:
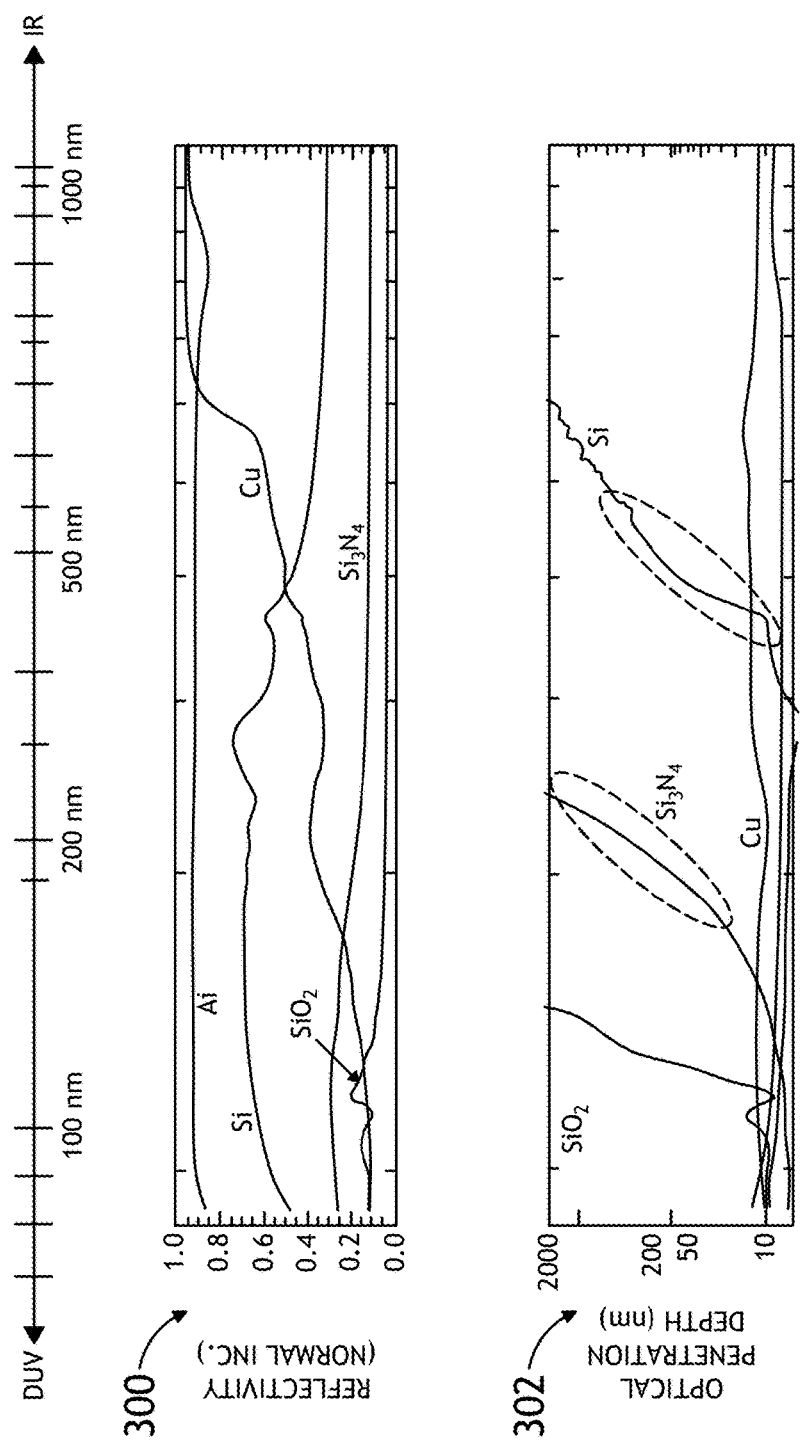
FIG. 3A is a chart showing reflectivity and optical penetration at different wavelengths for a plurality of materials.
Figure 3B:
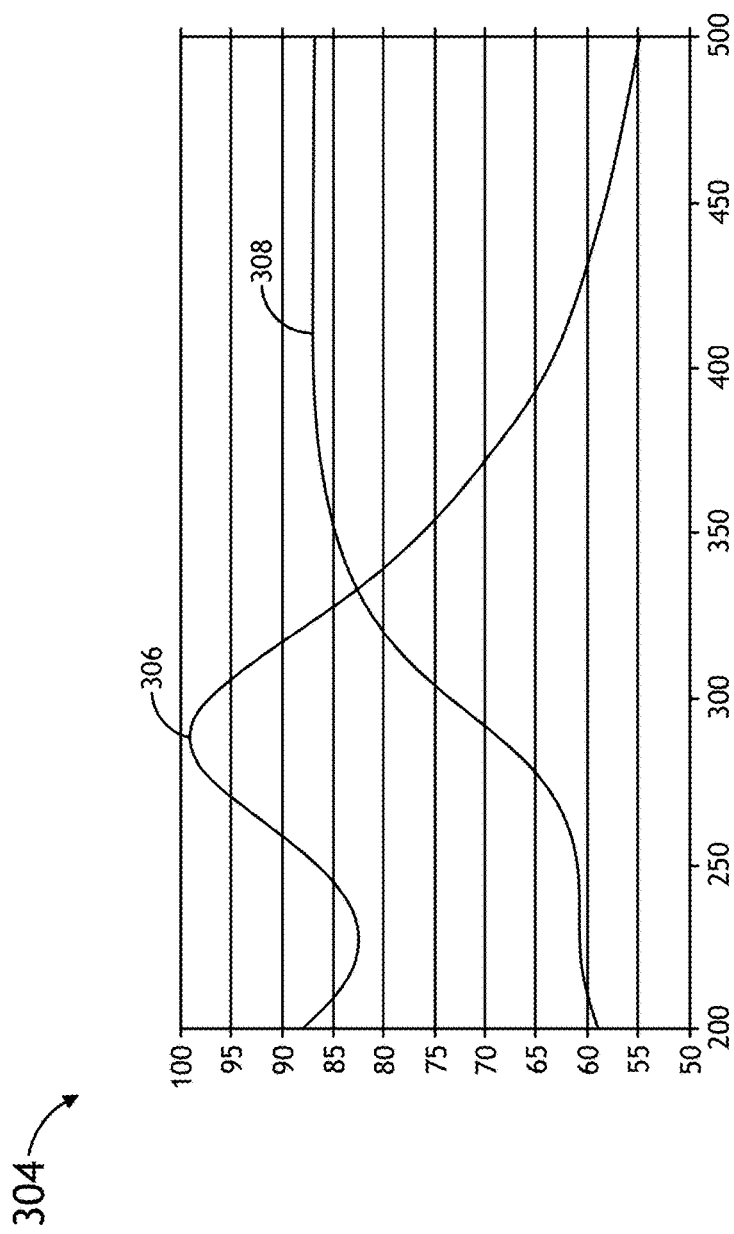
FIG. 3B is a chart showing reflectivity at different wavelengths for a first layer of sample and a second layer of a sample, in accordance with an embodiment of this disclosure.
Figure 3C:
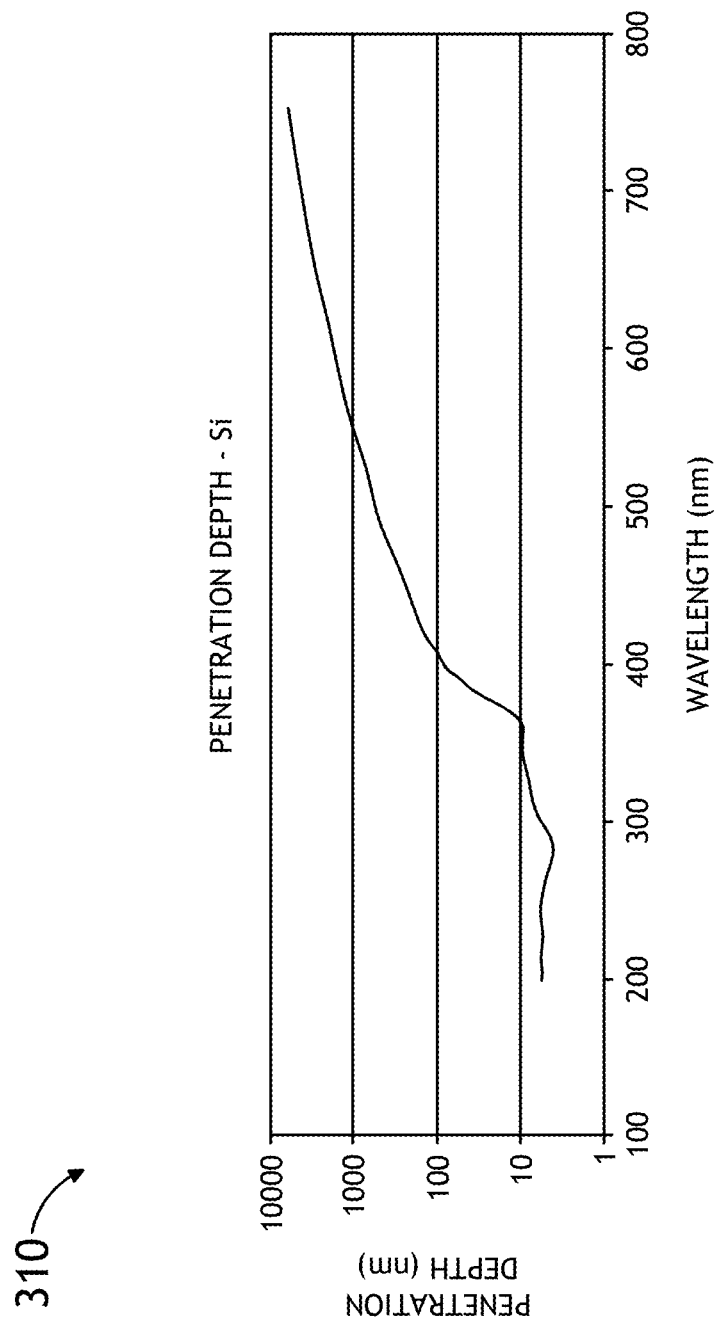
FIG. 3C is a chart showing optical penetration at different wavelengths for silicon.

As shown in FIG. 3A, reflectivity and optical penetration of certain materials may vary significantly at different wavelengths. For example, as can be seen in chart 300, copper (Cu) exhibits much higher reflectivity at longer wavelengths. Some materials may be substantially opaque over certain wavelengths and substantially transparent or translucent at other wavelengths. For example, as can be seen in chart 302, the optical penetration curves for $SiO_2$, $Si_3N_4$, and Si show rapid inclines over narrow ranges of illumination spectra. Chart 310 in FIG. 3C further illustrates the penetration depth of silicon (Si) as a function of wavelength. Because of the difference in reflectivity and/or optical penetration of various materials at different wavelengths, the first and second wavelengths or bands of illumination may be utilized to inspect different layers of the sample 101. As shown in chart 304 of FIG. 3B, a reflectivity curve 306 associated with a first layer of the sample 101 and a reflectivity curve 308 associated with a second layer of the sample 101 may increase and decrease over different ranges of illumination spectra. As a result, the first imaging path 116 may be configured to receive illumination reflected, scattered, or radiated more strongly from the first layer of the sample 101, and the second imaging path 120 may be configured to receive illumination reflected, scattered, or radiated more strongly from the second layer (e.g. a previous layer) of the sample 101, or vice versa.

In some embodiments, the computing system 134 may be configured to combine and/or compare the imaging data collected (primarily) from the first layer via the first imaging path 116 and the imaging data collected (primarily) from the second layer via the second imaging path 120 to detect and/or analyze DOI located in at least one of the sample layers. The computing system 134 may be further configured to fuse the images collected via the parallel imaging paths 116 and 120 into a three-dimensional image of a selected portion of the sample 101 including at least a portion of the first layer and at least a portion of the second layer. Additionally or alternatively, the computing system 134 may be configured to compare the imaging data collected via the first imaging path 116 and the imaging data collected via the second imaging path 120 to differentiate image components attributable to one or more sample defects located in the first layer from image components attributable to one or more sample defects located in the second layer. For example, the imaging data collected via the first imaging path 116 may include stronger image components associated with first layer defects, while the imaging data collected via the second imaging path 120 may include stronger components associated with second layer defects. The computing system 134 may be further configured to isolate DOI (e.g. current layer defects) by excluding image components attributable to defects included in another layer (e.g. previous layer defects).

Some occasions may necessitate or further accuracy may be gained by running multiple inspection passes or swaths. When imaging data is collected via the first and second imaging paths 116 and 120 at a first time and at least a second time, the computing system 134 may be further configured to align the imaging data collected with each inspection pass utilizing one of the imaging paths as a reference path. For example, the computing system 134 may be configured to utilize imaging data collected via the second imaging path 120 as a common reference (e.g. similar detected features or image components) for aligning the imaging data collected via the first imaging path 116 at the first time with the imaging data collected via the first imaging path 116 at the second time. For example, the computing system 134 may be configured to determine an offset between image components or features detected via the second imaging path 120 at the first and second times. The computing system 134 may then combine the imaging data collected via the first imaging path 116 at the first and second times utilizing the determined offset to assist alignment of the images collected with the different inspection passes.

Figure 4A:
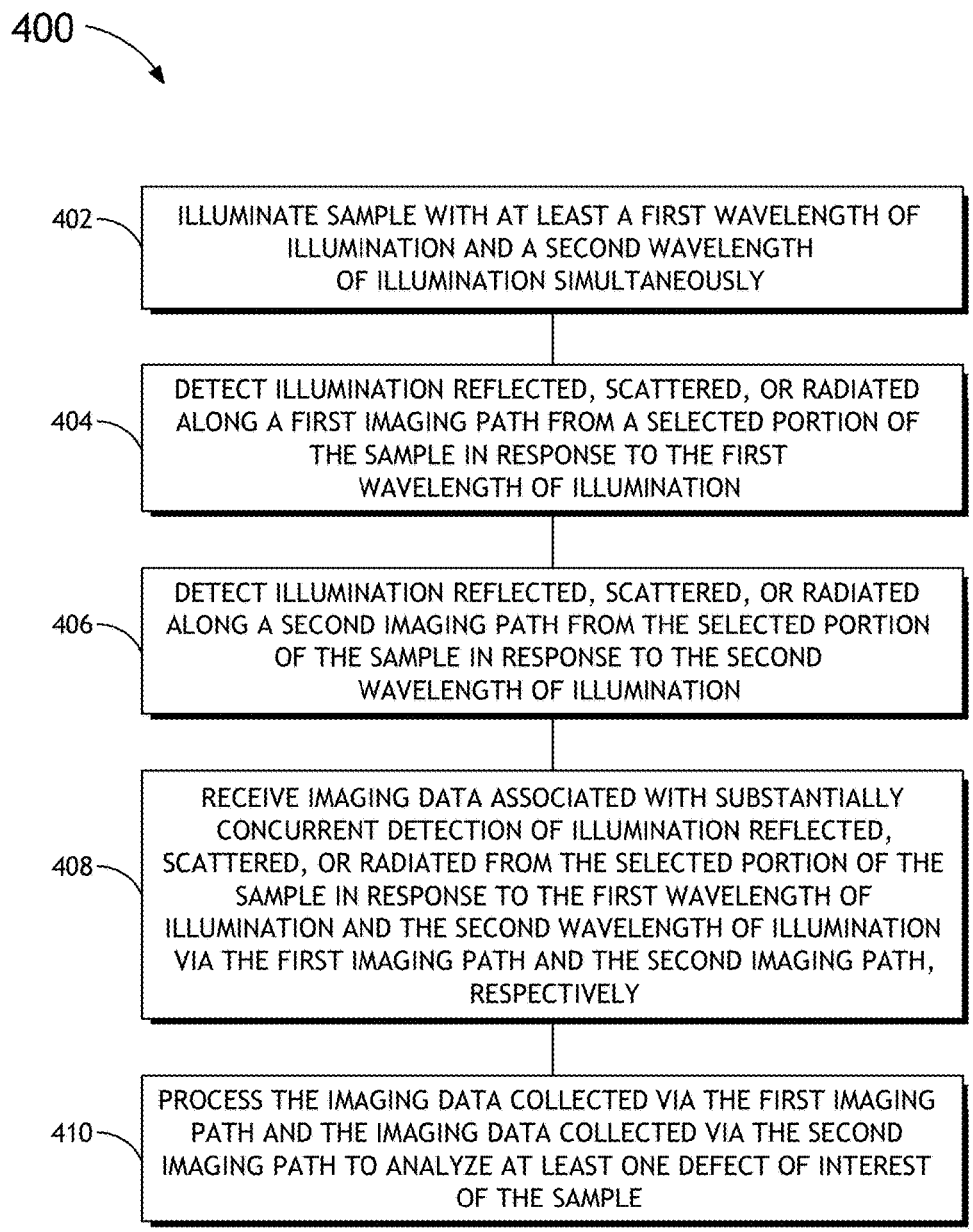
FIG. 4A is a flow diagram illustrating a method of inspecting a sample with multiple wavelengths of illumination simultaneously via parallel imaging paths, in accordance with an embodiment of this disclosure.
Figure 4B:
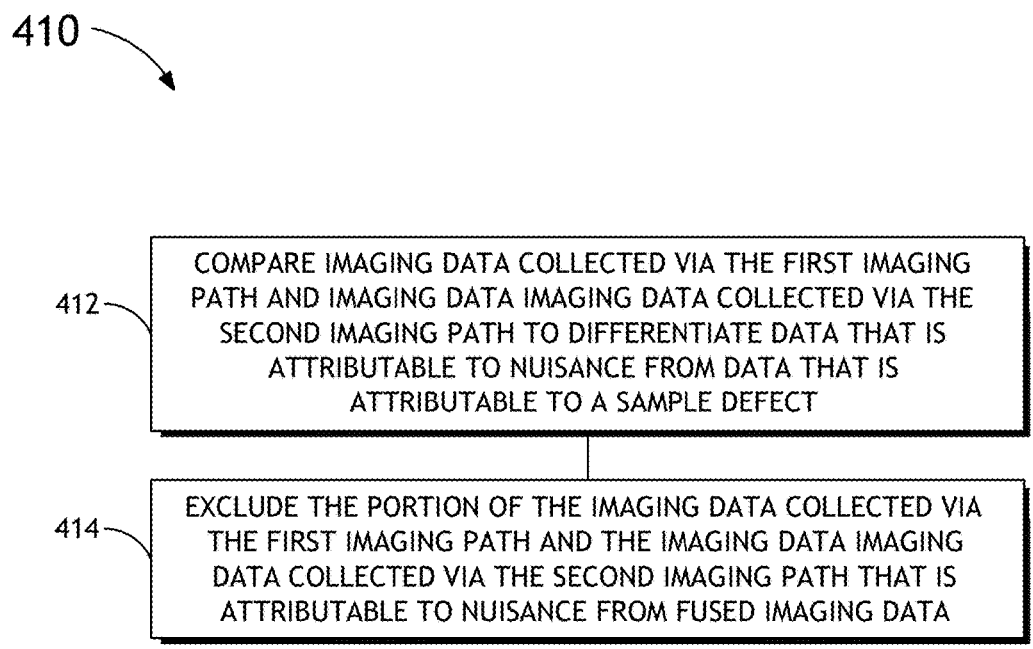
FIG. 4B is a flow diagram illustrating steps for processing imaging data collected via two or more parallel imaging paths, in accordance with an embodiment of this disclosure.
Figure 4C:
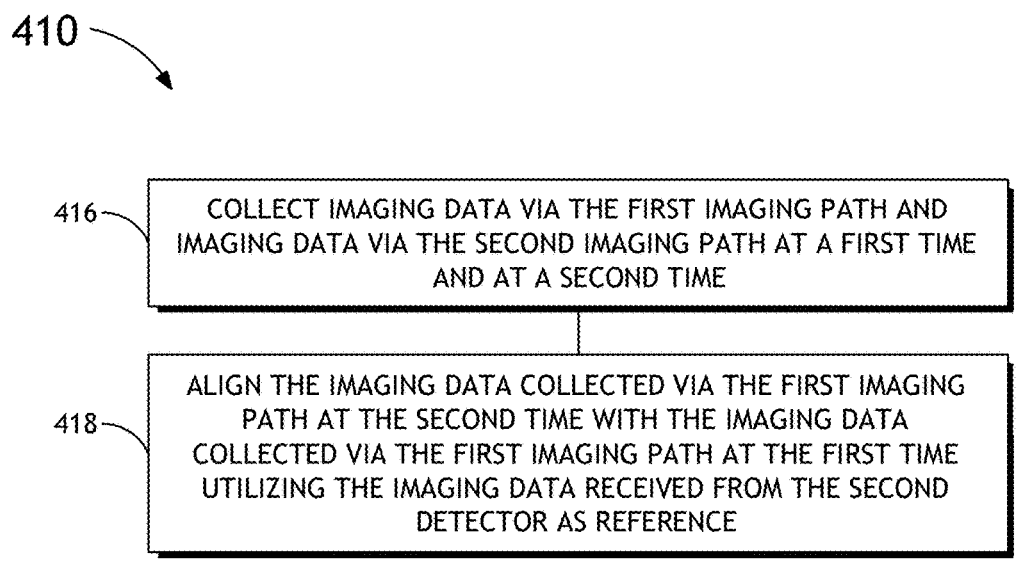
FIG. 4C is a flow diagram illustrating steps for processing imaging data collected via two or more parallel imaging paths, in accordance with an embodiment of this disclosure.

FIGS. 4A through 4C are flow diagrams illustrating an embodiment of a method 400 of inspecting a sample with multiple wavelengths of illumination simultaneously via parallel imaging paths. The method 400 may be manifested by an embodiment of system 100. For example, various steps of method 400 may carried out via one or more structural components of system 100 and/or implemented via one or more instruction sets embedded in the program instructions 138 executed by the computing system 134. Method 400 may further include steps for performing one or more of the functions or operations described above with regard to one or more embodiments of system 100. However, method 400 is not limited by the embodiments of system 100 described herein and may be carried out by any system configured to perform one or more of the following steps.

Looking now to FIG. 4A, a sample is inspected utilizing multiple wavelengths or bands of illumination detectable in parallel with at least a first imaging path and a second imaging path. At step 402, the sample is illuminated with at least a first wavelength or band of illumination and a second wavelength or band of illumination (different from the first). The illumination may be provided via one or more illumination sources, such as a broadband source or multiple single/narrow band sources. At steps 404 and 406, illumination reflected, scattered, or radiated from a selected portion of the sample in response to the first wavelength/band of illumination and illumination reflected, scattered, or radiated from the selected portion of the sample in response to the second wavelength/band of illumination are detected in parallel via a first imaging path and a second imaging path, respectively. In some embodiments, the imaging paths are further split into multiple modes, such as a first imaging mode and a second imaging mode, based upon wavelength, polarization, aperture settings, or the like. At step 408, imaging data based upon the illumination detected in parallel via the first and second imaging paths is received by a computing system. The computing system then processes the imaging data at step 410 to detect and/or analyze at least one DOI.

In some embodiments, as shown in FIG. 4B, the processing at step 410 may include step 412 of comparing the imaging data collected via the first imaging path and the imaging data collected via the second imaging path to differentiate nuisance components of the data from data components that are attributable to the defect of interest. At step 414, the nuisance components of the data may be excluded from fused imaging data including at least a portion of the data collected via the first imaging path and at least a portion of the data collected via the second imaging path. In some embodiments, the nuisance components are not isolated and removed but, nevertheless, reduced by averaging the imaging data collected via the first imaging path and the imaging data collected via the second imaging path.

When multiple inspection passes are performed, data collected via one of the imaging paths at a first time may be fused with data collected via the same imaging path as a second time. As shown in FIG. 4C, the processing at step 410 may include step 416 of collecting imaging data via the first imaging path and the second imaging path at a first time and at least a second time. At step 418, the imaging data collected via one of the imaging paths (e.g. the second imaging path) may be utilized as reference for alignment of the imaging data collected via the other imaging path (e.g. the first imaging path) at the first and second times. For example, a spatial offset between features or image components detected in first and second time images with the second imaging path may be determined and utilized to assist alignment of images collected at the first and second times via the first imaging path. Accordingly, the imaging data collected via the first imaging path with multiple inspection passes can be effectively fused to further enhance DOI resolution.

Figure 4D:
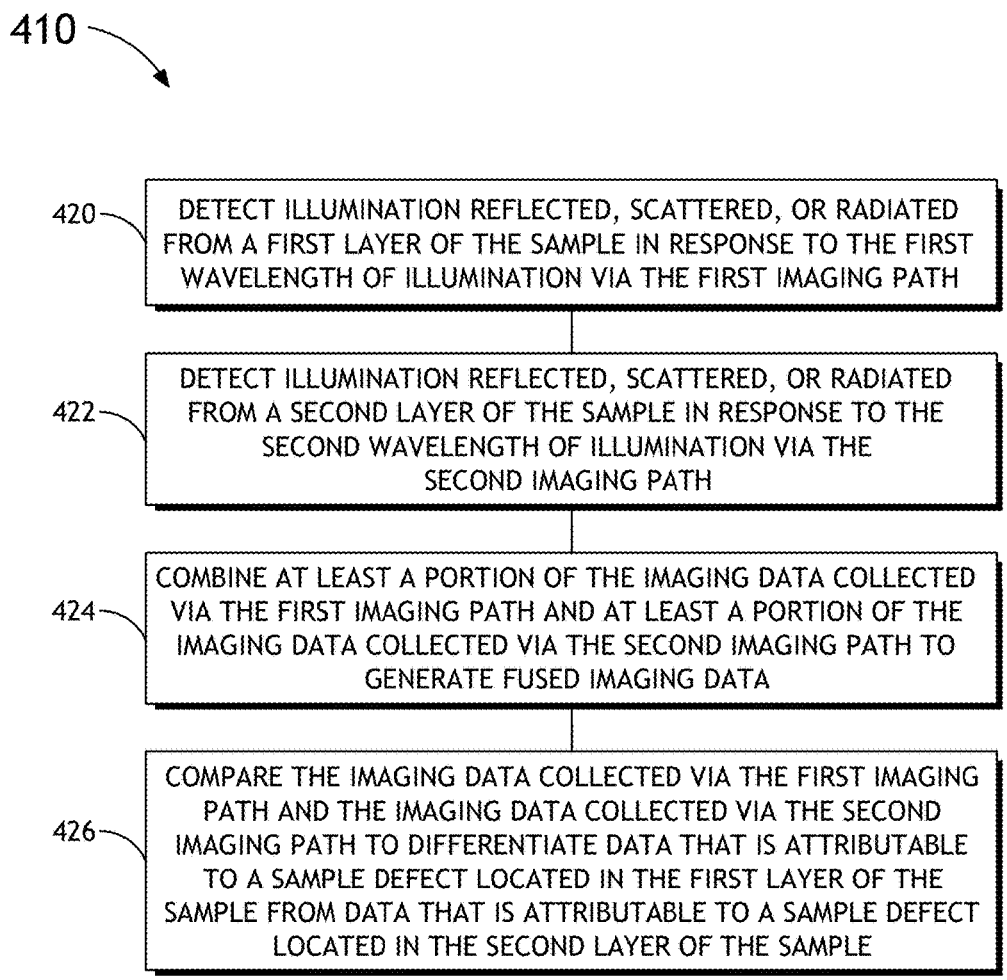
FIG. 4D is a flow diagram illustrating steps for processing imaging data collected via two or more parallel imaging paths, wherein imaging data is collected from two or more layers of a sample, in accordance with an embodiment of this disclosure.

As discussed above, reflectivity and/or optical penetration of device layers may vary as a function of wavelength. FIG. 4D illustrates an embodiment where the processing at step 410 takes advantage of the reflectance at each layer in response to the wavelength or band of illumination being used to image the layer. At steps 420 and 422, illumination reflected, scattered, or radiated (primarily) from a first layer of the sample in response to the first wavelength or band of illumination is detected via the first imaging path, and illumination reflected, scattered, or radiated (primarily) from a second layer of the sample in response to the second wavelength or band of illumination is detected via the second imaging path. At step 424, the resulting imaging data may be combined to generate fused imaging data including at least a portion of imaging data associated with the first layer of the sample and at least a portion of imaging data associated with the second layer of the sample. In some embodiments, the fused imaging data may include a three-dimensional image of a selected portion of the sample including a portion of the first layer and a portion of the second layer. The fused imaging data may be analyzed to detect and/or measure one or more parameters of one or more DOI located in the first layer and/or the second layer of the sample. For example, first layer DOI identified utilizing the imaging data collected via the first imaging path (primarily from the first layer) in response to the first wavelength/band of illumination and second layer DOI identified utilizing the imaging data collected via the second imaging path (primarily from the second layer) in response to the second wavelength/band of illumination may be represented in the fused imaging data.

The processing at step 410 may additionally or alternatively include step 426, where the imaging data collected via the first imaging path (primarily from the first layer) and the imaging data collected via the second imaging path (primarily from the second layer) are compared to differentiate image components attributable to one or more sample defects located in the first layer from image components attributable to one or more sample defects located in the second layer. Accordingly, the first layer or second layer defects may be detected or analyzed with greater clarity by excluding image components associated with one of the layers. For example, image components attributable to DOI located in the first layer (e.g. current layer) may be isolated by excluding image components attributable to a sample defect located in the second layer (e.g. previous layer). Imaging data collected via each path may include image components attributable to both sample defects of the first layer and the second layer. However, the image components attributable to second layer defects may be stronger in the imaging data collected via the second imaging path, while image components attributable to first layer defects may be stronger in the imaging data collected via the first imaging path. Thus, the first layer defects and the second layer defects can be differentiated and isolated from one another by excluding image components attributable to the sample defects located in one of the layers, separately from first and second imaging data or filtered out of the fused imaging data.

Noise and nuisances frequently overwhelm the identification of DOI. Comparing images from multiple acquisitions under different imaging conditions enables improved differentiation of noise/nuisances from the DOI. However, if the images are obtained at different times, then it is very difficult to align them and fuse the information together. According to various embodiments of the system 100 and method 400 described herein, simultaneous (i.e. single pass) inspection with multiple wavelengths or bands of illumination is enabled. Moreover, when multiple passes/swaths are required or performed to achieve an enhanced data set, the system 100 described above provides mechanisms to better align the images and make image fusion more effective. Those having skill in the art will appreciate the advantages provided by the embodiments illustrated and described herein and that further advantages may be gained by combining or modifying the foregoing embodiments.

Those having skill in the art will further appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. In some embodiments, various steps, functions, and/or operations are carried out by one or more of the following: electronic circuits, logic gates, multiplexers, ASICs, multiplexers, field programmable gate arrays, or computing systems. A computing system may include, but is not limited to, a personal computing system, mainframe computing system, workstation, image computer, parallel processor, or any other device known in the art. In general, the term "computing system" is broadly defined to encompass any device having one or more processors, which execute instructions from a carrier medium. Program instructions implementing methods such as those described herein may be transmitted over or stored on carrier media. A carrier medium may include a transmission medium such as a wire, cable, or wireless transmission link. The carrier medium may also include a storage medium such as a read-only memory, a random access memory, a magnetic or optical disk, or a magnetic tape.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

What is claimed is:

1. A system for inspecting a sample with multiple wavelengths of illumination, comprising:
   one or more illumination sources configured to illuminate at least a selected portion of a sample with at least a first wavelength of illumination selectable from a first spectral band and a second wavelength of illumination selectable from a second spectral band, wherein the second wavelength of illumination is different from the first wavelength of illumination, wherein the first wavelength of illumination is reflected, scattered, or radiated by at least a first layer comprised of a first material of the sample and is transmitted by at least a second layer comprised of a second material of the sample, wherein the second wavelength of illumination is reflected, scattered, or radiated by the at least the second layer of the sample;
   a first detector including one or more imaging sensors configured to detect illumination reflected, scattered, or radiated along a first imaging path from the selected portion of the sample in response to the first wavelength of illumination;
   a second detector including one or more imaging sensors configured to detect illumination reflected, scattered, or radiated along a second imaging path from the selected portion of the sample in response to the second wavelength of illumination; and
   a computing system communicatively coupled with the one or more imaging sensors of the first detector and the one or more imaging sensors of the second detector, wherein the computing system is configured to:
      receive imaging data from the first detector for a first inspection pass and a second inspection pass;
      receive imaging data from the second detector for the first inspection pass and the second inspection pass;
      align the imaging data received from the first detector for the first inspection pass and the second inspection pass, wherein the imaging data received from the second detector for the first inspection pass and the second inspection pass is utilized as a reference for the alignment; and
      compare the imaging data received from the first detector for the first inspection pass and the second inspection pass to differentiate a portion of the imaging data received from the first detector for the first inspection pass and the second inspection pass that is attributable to nuisance from a portion of the imaging data received from the first detector for the first inspection pass and the second inspection pass that is attributable to a sample defect of interest.

2. The system of claim 1, wherein the computing system is further configured to:
   generate fused imaging data from the aligned imaging data received from the first detector for the first inspection pass and the second inspection pass; and
   exclude the portion of the imaging data received from the first detector for the first inspection pass and the second inspection pass that is attributable to nuisance from the fused imaging data.

3. The system of claim 1, wherein the at least the first material of the sample is opaque at the first wavelength of illumination, wherein the at least the second material of the sample is translucent at the first wavelength of illumination and opaque at the second wavelength of illumination, wherein a reflectance of the first wavelength of illumination at the first layer of the sample is greater than a reflectance of the second wavelength of illumination at the first layer of the sample.

4. The system of claim 3, wherein the computing system is further configured to:
   combine at least a portion of the imaging data received from the first detector and at least a portion of the imaging data received from the second detector to generate fused imaging data including imaging data associated with a sample defect of interest located in at least one of the first and second layers of the sample.

5. The system of claim 3, wherein the computing system is further configured to:
   compare the imaging data received from the first detector and the imaging data received from the second detector to differentiate a portion of the imaging data received from the first detector and the imaging data received from the second detector that is attributable to a sample defect located in the first layer of the sample from a portion of the imaging data received from the first detector and the imaging data received from the second detector that is attributable to a sample defect located in the second layer of the sample.

6. The system of claim 1, wherein the second spectral band is different from the first spectral band.

7. The system of claim 1, wherein the one or more illumination sources include at least a first illumination source configured to illuminate the sample with the first wavelength of illumination via a first illumination path and a second illumination source configured to illuminate the sample with the second wavelength of illumination via a second illumination path.

8. The system of claim 7, further comprising:
   at least one dichroic combiner configured to direct illumination emanating from the first illumination source and illumination emanating from the second illumination source along a common illumination path leading to the surface of the sample.

9. The system of claim 7, further comprising:
   at least one beam splitter configured to transmit illumination emanating from at least one of the first illumination source and the second illumination source to the surface of the sample according to a first imaging mode and a second imaging mode.

10. The system of claim 9, wherein the first imaging mode and the second imaging mode are associated with one or more of: different wavelengths of illumination, different polarizations, and different aperture settings.

11. The system of claim 9, wherein the first detector is configured to concurrently detect illumination reflected, scattered, or radiated along the first imaging path from the selected portion of the sample according the first imaging mode and the second imaging mode, and wherein the second detector is configured to detect illumination reflected, scattered, or radiated along the second imaging path from the selected portion of the sample according to the first imaging mode and the second imaging mode.

12. The system of claim 1, further comprising:
at least one dichroic splitter configured to direct illumination reflected, scattered, or radiated from the selected portion of the sample in response to the first wavelength of illumination along the first imaging path and further configured to direct illumination reflected, scattered, or radiated from the selected portion of the sample in response to the second wavelength of illumination along the second imaging path.

13. The system of claim 1, further comprising:
an autofocus module configured to detect illumination reflected, scattered, or radiated along a third imaging path from the selected portion of the sample in response to a third wavelength of illumination.

14. The system of claim 13, wherein the one or more illumination sources include at least a first illumination source configured to illuminate the sample with the first wavelength of illumination via a first illumination path and a second illumination source configured to illuminate the sample with the second wavelength of illumination and the third wavelength of illumination via a second illumination path, wherein the second wavelength of illumination and the third wavelength of illumination is longer than the first wavelength of illumination.

15. The system of claim 14, wherein the first illumination source or the second illumination source comprises a broadband illumination source.

16. The system of claim 14, wherein the first illumination source comprises a broadband illumination source and the second illumination source comprises a broadband illumination source.

17. The system of claim 1, wherein a difference between the first wavelength and the second wavelength is at least 300 nm.

18. A method of inspecting a sample with multiple wavelengths of illumination, comprising:
illuminating at least a selected portion of a sample with at least a first wavelength of illumination selectable from a first spectral band and a second wavelength of illumination selectable from a second spectral band, wherein the second wavelength of illumination is different from the first wavelength of illumination, wherein the first wavelength of illumination is reflected, scattered, or radiated by at least a first layer comprised of a first material of the sample and is transmitted by at least a second layer comprised of a second material of the sample, wherein the second wavelength of illumination is reflected, scattered, or radiated by the at least the second layer of the sample;
detecting illumination reflected, scattered, or radiated along a first imaging path from the selected portion of the sample in response to the first wavelength of illumination for a first inspection pass and a second inspection pass;
detecting illumination reflected, scattered, or radiated along a second imaging path from the selected portion of the sample in response to the second wavelength of illumination for the first inspection pass and the second inspection pass;
aligning the imaging data collected via the first imaging path for the first inspection pass and the second inspection pass, wherein the imaging data collected via the second imaging path for the first inspection pass and the second inspection pass is utilized as a reference for the alignment; and
comparing the imaging data collected via the first imaging path for the first inspection pass and the second inspection pass to differentiate a portion of the imaging data collected via the first imaging path for the first inspection pass and the second inspection pass that is attributable to nuisance from a portion of the imaging data collected via the first imaging path for the first inspection pass and the second inspection pass that is attributable to a sample defect of interest.

19. The method of claim 18, further comprising:
generating fused imaging data from the aligned imaging data collected via the first imaging path for the first inspection pass and the second inspection pass; and
excluding the portion of the imaging data collected via the first imaging path for the first inspection pass and the second inspection pass that is attributable to nuisance from the fused imaging data.

20. The method of claim 18, wherein the at least the first material of the sample is opaque at the first wavelength of illumination, wherein the at least the second material of the sample is translucent at the first wavelength of illumination and opaque at the second wavelength of illumination, wherein a reflectance of the first wavelength of illumination at the first layer of the sample is greater than a reflectance of the second wavelength of illumination at the first layer of the sample.

21. The method of claim 20, further comprising:
combining at least a portion of the imaging data collected via the first imaging path and at least a portion of the imaging data collected via the second imaging path to generate fused imaging data including imaging data associated with a sample defect of interest located in at least one of the first and second layers of the sample.

22. The method of claim 20, further comprising:
comparing the imaging data collected via the first imaging path and the imaging data collected via the second imaging path to differentiate a portion of the imaging data collected via the first imaging path and the imaging data collected via the second imaging path that is attributable to a sample defect located in the first layer of the sample from a portion of the imaging data collected via the first imaging path and the imaging data collected via the second imaging path that is attributable to a sample defect located in the second layer of the sample.

23. The method of claim 18, further comprising:
splitting illumination directed to the surface of the sample according to a first imaging mode and a second imaging mode.

24. The method of claim 23, wherein the first imaging mode and the second imaging mode are associated with one or more of: different wavelengths of illumination, different polarizations, and different aperture settings.

25. The method of claim 23, further comprising:
concurrently detecting illumination reflected, scattered, or radiated along the first imaging path from the selected portion of the sample according to the first imaging mode and the second imaging mode; and concurrently detecting illumination reflected, scattered, or radiated along the second imaging path from the selected portion of the sample according to the first imaging mode and the second imaging mode.

26. A system for inspecting a sample with multiple wavelengths of illumination, comprising:
- a first illumination source configured to illuminate at least a selected portion of a sample with a first wavelength of illumination, wherein the first wavelength of illumination is selectable from a first spectral band, wherein the first wavelength of illumination is reflected, scattered, or radiated by at least a first layer comprised of a first material of the sample and is transmitted by at least a second layer comprised of a second material of the sample;
- a second illumination source configured to illuminate at least a portion of the sample with a second wavelength of illumination and a third wavelength of illumination, wherein the second and third wavelengths of illumination are longer than the first wavelength of illumination, wherein the second and third wavelengths are selectable from at least a second spectral band, wherein the second wavelength of illumination is reflected, scattered, or radiated by the at least the second layer of the sample;
- a first detector including one or more imaging sensors configured to detect illumination reflected, scattered, or radiated along a first imaging path from the selected portion of the sample in response to the first wavelength of illumination;
- a second detector including one or more imaging sensors configured to detect illumination reflected, scattered, or radiated along a second imaging path from the selected portion of the sample in response to the second wavelength of illumination;
- an autofocus module configured to detect illumination reflected scattered, or radiated along a third imaging path from the selected portion of the sample in response to the third wavelength of illumination, wherein the second imaging path and the third imaging path share one or more optical elements; and
- a computing system communicatively coupled with the one or more imaging sensors of the first detector and the one or more imaging sensors of the second detector, wherein the computing system is configured to:
  - receive imaging data from the first detector for a first inspection pass and a second inspection pass;
  - receive imaging data from the second detector for the first inspection pass and the second inspection pass; and
  - align the imaging data received from the first detector for the first inspection pass and the second inspection pass, wherein the imaging data received from the second detector for the first inspection pass and the second inspection pass is utilized as a reference for the alignment,
  - wherein the imaging data from the first detector and the imaging data from the second detector are associated with concurrent detection of illumination reflected, scattered, or radiated from the selected portion of the sample in response to the first wavelength of illumination and the second wavelength of illumination via the first imaging path and the second imaging path, respectively.

27. The system of claim 26, wherein the computing system is further configured to:
- compare the imaging data received from the first detector for the first inspection pass and the second inspection pass to differentiate a portion of the imaging data received from the first detector for the first inspection pass and the second inspection pass that is attributable to nuisance from a portion of the imaging data received from the first detector for the first inspection pass and the second inspection pass that is attributable to a sample defect of interest.

28. The system of claim 27, wherein the computing system is further configured to:
- generate fused imaging data from the aligned imaging data received from the first detector for the first inspection pass and the second inspection pass; and
- exclude the portion of the imaging data received from the first detector for the first inspection pass and the second inspection pass that is attributable to nuisance from the fused imaging data.

29. The system of claim 26, wherein the at least the first material of the sample is opaque at the first wavelength of illumination, wherein the at least the second material of the sample is translucent at the first wavelength of illumination and opaque at the second wavelength of illumination, wherein a reflectance of the first wavelength of illumination at the first layer of the sample is greater than a reflectance of the second wavelength of illumination at the first layer of the sample.

30. The system of claim 29, wherein the computing system is further configured to:
- combine at least a portion of the imaging data received from the first detector and at least a portion of the imaging data received from the second detector to generate fused imaging data including imaging data associated with a sample defect of interest located in at least one of the first and second layers of the sample.

31. The system of claim 29, wherein the computing system is further configured to:
- compare the imaging data received from the first detector and the imaging data received from the second detector to differentiate a portion of the imaging data received from the first detector and the imaging data received from the second detector that is attributable to a sample defect located in the first layer of the sample from a portion of the imaging data received from the first detector and the imaging data received from the second detector that is attributable to a sample defect located in the second layer of the sample.

32. The system of claim 26, wherein the autofocus module is configured for pre-inspection of the sample.

* * * * *